(12) United States Patent
Umemoto et al.

(10) Patent No.: US 8,019,473 B2
(45) Date of Patent: Sep. 13, 2011

(54) MANIPULATOR AND METHOD OF CONTROLLING MANIPULATOR

(75) Inventors: Yoshitaka Umemoto, Hachioji (JP); Kazuhiko Takahashi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 372 days.

(21) Appl. No.: 12/423,289

(22) Filed: Apr. 14, 2009

(65) Prior Publication Data

US 2009/0259340 A1  Oct. 15, 2009

(30) Foreign Application Priority Data

Apr. 15, 2008  (JP) ................................. 2008-105975

(51) Int. Cl.
G05B 19/04 (2006.01)
G05B 19/18 (2006.01)
G05B 19/418 (2006.01)
G05B 19/408 (2006.01)
B25J 15/02 (2006.01)

(52) U.S. Cl. ................... 700/250; 700/247; 318/568.21; 318/568.22

(58) Field of Classification Search .................. 700/245, 700/247, 250, 258, 259, 262; 318/568.11, 318/568.2, 568.21, 568.22; 901/9, 15, 28, 901/46
See application file for complete search history.

(56) References Cited

U.S. PATENT DOCUMENTS

| 3,845,370 | A | | 10/1974 | Mantey | |
|---|---|---|---|---|---|
| 4,618,885 | A | | 10/1986 | Nagasaki et al. | |
| 5,581,166 | A | * | 12/1996 | Eismann et al. | 318/568.22 |
| 6,091,219 | A | | 7/2000 | Maruo et al. | |
| 7,245,225 | B2 | * | 7/2007 | Kamio et al. | 340/648 |
| 7,328,120 | B2 | * | 2/2008 | Hirabayashi | 702/141 |
| 2004/0193015 | A1 | | 9/2004 | Ikeda et al. | |
| 2005/0099153 | A1 | | 5/2005 | Komatsu et al. | |
| 2007/0013336 | A1 | * | 1/2007 | Nowlin et al. | 318/568.21 |
| 2010/0168919 | A1 | * | 7/2010 | Okamoto | 700/275 |

FOREIGN PATENT DOCUMENTS

| EP | 0 809 163 A2 | 11/1997 |
|---|---|---|
| EP | 2110212 A2 * | 10/2009 |
| JP | 07-237174 | 9/1995 |
| JP | 10-315173 | 12/1998 |
| JP | 2002-315719 | 10/2002 |
| JP | 2003-230536 | 8/2003 |
| JP | 2004-290548 | 10/2004 |
| JP | 2007-222671 | 9/2007 |
| WO | WO 2004/071718 A1 | 8/2004 |

OTHER PUBLICATIONS

Japanese Office Action dated Jun. 22, 2010.
Extended European Search Report dated Nov. 29, 2010.

* cited by examiner

*Primary Examiner* — Crystal J Barnes-Bullock
(74) *Attorney, Agent, or Firm* — Scully, Scott Murphy & Presser, P.C.

(57) ABSTRACT

A manipulator includes: a drive section which electrically drives a joint; an instruction input section which executes instruction input; a control section which generates a driving signal in response to the instruction input; a sensor which detects an operation status of the joint or the drive section in time series; a setting section which sets an allowable operation range of the drive section; a determination section which determines whether an operation status signal including a detection signal is within the allowable operation range; and a replacement section which, in a case when the operation status signal is determined as deviating from the allowable operation range, replaces the detection signal with a previous detection signal acquired just before the determination of deviance in order to generate a driving signal.

24 Claims, 9 Drawing Sheets

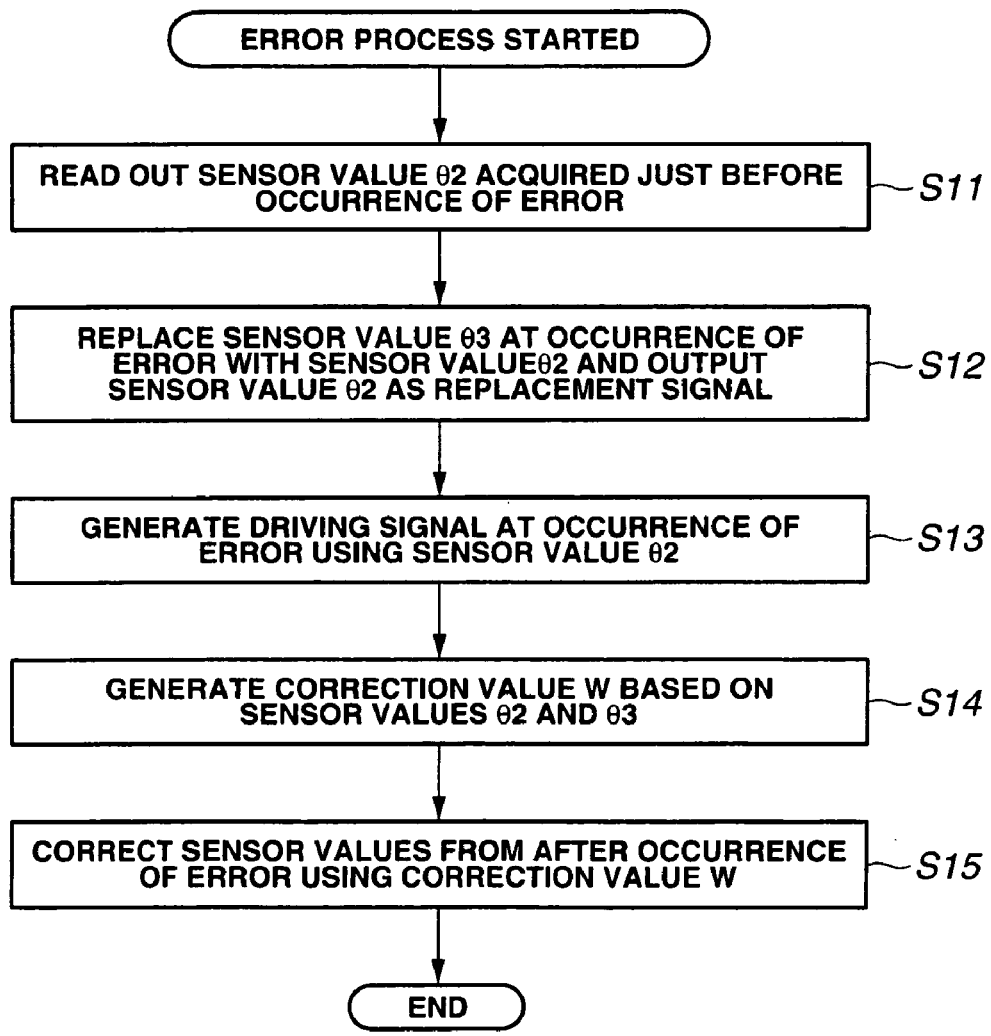

MANIPULATOR AND METHOD OF CONTROLLING MANIPULATOR

This application claims benefit of Japanese Application No. 2008-105975 filed in Japan on Apr. 15, 2008, the contents of which are incorporated by this reference.

BACKGROUND OF THE INVENTION

1. Field of the Invention

The present invention relates to a manipulator for driving a turnable joint.

2. Description of the Related Art

An endoscope which is capable of monitoring inside a body and performing appropriate treatments using treatment instruments where necessary has been used widely in the medical field. The endoscope usually has a bending section, configured as having a plurality of joints being connected in a turnable manner, at a distal end side of its insertion section in order to be able to be easily inserted into a flexural body.

One type of an endoscope would be a hand-operated type in which the bending section is bend-driven through manual operation (where operating force is required). An electromotive bending type endoscope has also been put to practical use. In the electromotive bending type endoscope, that is, a type that has a manipulator, electrical driving means such as a motor is used in bend-driving the bending section for the purpose of further enhancing operability.

With respect to a treatment instrument as well, some instruments have achieved further enhanced operability by adopting a manipulator which is configured to drive the bending section having a plurality of joints by driving means such as a motor through an instructing operation on a proximal side.

As one example in the prior art, for instance, Japanese Patent Application Laid-Open Publication No. 10-315173 discloses a device having a secondary filter as being a modeled position control section as well as a position control model section where positional instruction is received; and malfunction detecting means configured as including the secondary filter, a comparator, an absolute value transforming section, and a subtractor, the malfunction detecting means functioning to compare an output signal from the position control model section with a position signal indicating an actual position of an electrical motor that drives a robot, and thus detect malfunction in the robot when a difference between the compared two signals becomes equal to or greater than a predetermined value.

With this device, when a difference between a signal from an input system and an output signal at a time when the electrical motor is driven in response to the input signal from the input system is equal to or greater than a predetermined value, it is determined that there is malfunction in the robot, whereby possible malfunction can be found in an early stage where further runaway of the robot can be stopped.

SUMMARY OF THE INVENTION

According to an aspect of the present invention, a manipulator includes: a drive section which electrically drives a turnable joint; an instruction input section which executes instruction input for rotating the joint; a driving signal generation section which generates a driving signal for driving the drive section in response to the instruction input; a sensor which detects an operation status of the joint or the drive section in time series; a setting section which sets an allowable operation range within which the drive section is operable in a case when the drive section is driven with the driving signal; a determination section which determines whether an operation status signal corresponding to the operation status is within the allowable operation range, the operation status signal at least including a detection signal detected by the sensor; a control section which, in a case when the operation status signal is determined as being within the allowable operation range, generates a driving signal for a time after the determination using the detection signal; and a replacement section which, in a case when the operation status signal is determined as deviating from the allowable operation range, replaces the detection signal with a previous detection signal having been determined as being within the allowable operation range just before a time the operation status signal has been determined as deviating from the allowable operation range, and generates a driving signal for a time after the determination of deviance.

According to an aspect of the present invention, a method of controlling a manipulator includes: an instruction input step for executing instruction input for rotating a turnable joint to a target angle; a first driving step for driving the joint via a drive section with a driving signal based on an instruction input signal from the instruction input step; a setting step for setting an allowable operation range allowed in a case of driving the joint; an acquiring step for acquiring, while the joint is rotating according to a driving signal, an angle of rotation of the joint as a sensor value in time series; a determining step for determining whether the sensor value acquired in the acquiring step is within the allowable operation range; and a second driving step in which, in a case when the sensor value is determined as being within the allowable operation range, a driving signal for a time after the determination is generated using the sensor value, and in a case when the sensor value is determined as deviating from the allowable operation range, a driving signal for a time after the determination is generated by replacing the sensor value with a previous sensor value having been determined as being within the allowable operation range just before the time when deviance is determined.

BRIEF DESCRIPTION OF THE DRAWINGS

FIG. 6 is a flow chart showing contents of processes in a case of error being determined;

DETAILED DESCRIPTION OF THE PREFERRED EMBODIMENTS

In the following, embodiments of the present invention will be described with reference to the attached drawings.

First Embodiment

Figure 1:
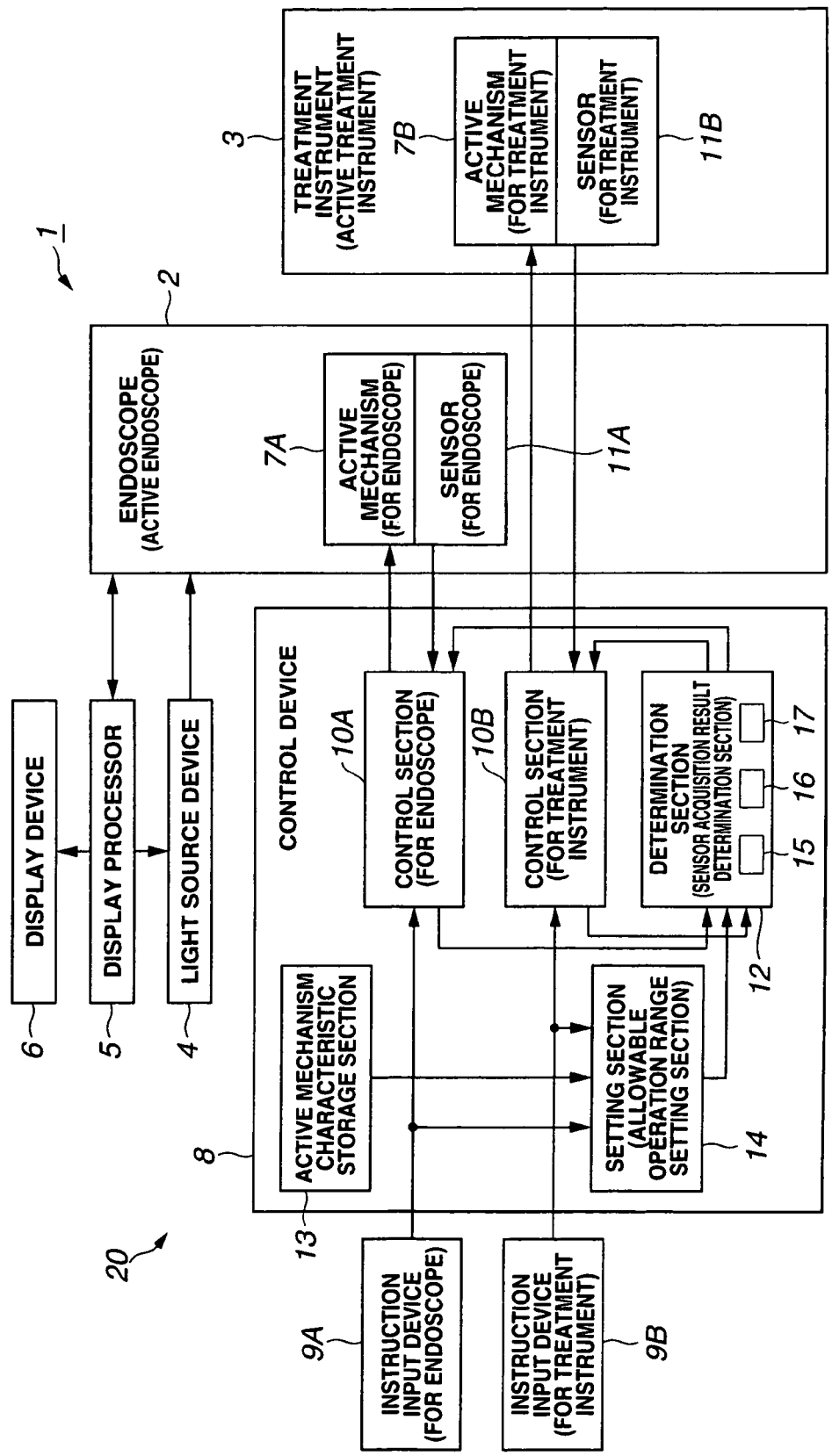
FIG. 1 is a block diagram showing an overall configuration of an endoscope treatment system that includes a first embodiment of the present invention.

FIG. 1 shows an endoscope treatment system (or an endoscope system) 1 that includes a manipulator according to a first embodiment of the present invention.

This endoscope treatment system 1 includes an active endoscope (hereinafter to be referred to simply as endoscope) 2; an active treatment instrument (hereinafter to be referred to simply as treatment instrument unless the term may sound confusing) 3 which is used along with the endoscope 2 and performs treatments; a light source device 4 which supplies the endoscope 2 with illuminating light, a display processor 5 which performs signal processing with respect to a signal from an image pickup section of the endoscope 2; and a display device 6 which displays an endoscope image that corresponds to an image signal from the display processor 5.

Moreover, the endoscope treatment system 1 includes a control device 8 which performs drive control on an endoscope active mechanism (to be referred to as active mechanism) 7A as arranged in the endoscope 2 and a treatment instrument active mechanism (to be referred to as active mechanism) 7B as arranged in the treatment instrument 3; and an endoscope instruction input device (to be referred to as instruction input device) 9A and a treatment instrument instruction input device (to be referred to as instruction input device) 9B which provides instruction inputs for driving the respective active mechanisms 7A and 7B. The active mechanisms 7A and 7B, in specific terms, are configured with motors as being rotary drive sections (drive sections in the broad sense) which actively (electrically) rotation-drive a bending section where joints are arranged.

The control device 8 includes an endoscope control section (to be referred to as control section) 10A which drives and controls the active mechanism 7A based on an instruction input from the instruction input device 9A and a treatment control section (to be referred to as control section) 10B which drives and controls the active mechanism 7B based on an instruction input value from the instruction input device 9B.

The active mechanisms 7A and 7B have an endoscope sensor (to be referred to as sensor unless the term may sound confusing) 11A and a treatment instrument sensor (to be referred to as sensor unless the term may sound confusing) 11B, respectively, which are attached to driving axes or the like, to serve as sensors to detect (or acquire as measured values) operation statuses (e.g. angles, or positions in the broad sense, indicating drive amounts) of the active mechanisms 7A and 7B. These sensors 11A and 11B may be encoders, for example, and detect rotation angles of the motors that configure the active mechanisms 7A and 7B.

The control device 8 (the control section 10I (I indicates A or B)) generates a driving signal for driving the active mechanism 7I being an instruction target based on an instruction input signal corresponding to a target driving angle having been inputted as an instruction input from the instruction input device 9I operated by an operator, and thus drives the active mechanism 7I.

Accordingly, the control section 10I functions as a driving signal generation section for producing (generating) a driving signal.

The operation status in terms of a driven angle of the active mechanism 7I as being driven based on the driving signal is detected (acquired) by the sensor 11I, and the detected sensor value is inputted to the control device (control section 10I) as a detection signal.

Thus, the active mechanism 7I is driven in time series (in time course) based on the driving signal that corresponds to the instruction input signal, while the operation status of the active mechanism 7I is detected and acquired as a sensor value by the sensor 11I in time series.

The control section 10I takes the detected sensor value as a control signal and subtracts the control signal from the instruction input signal to calculate a difference value (difference signal). Then the control section 10I takes the difference value as a new instruction input signal to generate a corresponding driving signal (i.e. a driving signal after the sensor value has been acquired), and thus controls the active mechanism 7I.

More specifically, when the active mechanism 7I is driven such that the angle thereof becomes the target driving angle indicated by the instruction input signal having been inputted as an instruction input, a resultant driven angle is detected by the sensor 11I, and then a difference value between the two signals (angles) is detected, on the basis of which the driving signal is feed-back controlled by the sensor value of the sensor 11I such that the difference value becomes "0".

By such feed-back control, the active mechanism 7I can be promptly set to the target driving angle having been inputted by the instruction input device 9I as the instruction input.

In this way, by such feed-back control, the active mechanism 7I can be controlled appropriately by a closed-loop. Moreover, in order to achieve further improved reliability, the control device 8, for example, is provided with a sensor acquisition result determination section (hereinafter to be referred to simply as determination section) 12 which acquires a sensor value, as being a detection signal, detected by the sensor 11I and determines whether the sensor value corresponds to an operation status signal that is in a normal state in terms of time.

Therefore, the determination section 12 takes in sensor values from both the sensors 11A and 11B through the control sections 10A and 10B, respectively. Meanwhile, it is also possible to arrange such that the determination section 12 takes in the sensor values directly from the sensors 11A and 11B not through the control sections 10A and 10B.

Furthermore, the control device 8, for example, is provided with an active mechanism characteristic storage section 13 where active mechanism characteristics (specifically, these active mechanism characteristics are: a rated output of the motor; operation parameters such as the maximum number of rotations; and parameters such as inertia moment, output voltage) that determine the characteristics of both the active mechanisms 7A and 7B are stored, and an allowable operation range setting section (to be referred to as setting section) 14 which sets an allowable operation range, defined as an operation range allowed to the active mechanism 7I within an operable range within which the active mechanism 7I is physically operable under a condition that the active mechanism 7I is driven based on operation parameters that can be specified by the active mechanism characteristics and the condition (information) indicated by the instruction input signal from the instruction input device 9I.

The determination section 12 allows the sensor values (i.e. data on angles as being sensor acquisition information) acquired by each sensor 11I to be stored in a memory section 15 in time series, and determines validity of an operation status signal, which at least includes the sensor value (angle in particular), by determining whether the operation status signal is within the allowable operation range based on the information about the allowable operation range having been outputted from the setting section 14.

That is, when the operation status signal is found to be within the allowable operation range, the determination section 12 determines that the operation status signal is normal or valid, whereas when the operation status signal is found to be deviating from the allowable operation range, the determination section 12 determines that the operation status signal is not valid due to problems such as noise, i.e. the determination section 12 determines that the operation status signal is in abnormal or in an error state. For instance, in a case where the operation status signal of the sensor value (angle) indicated by is deviating from the allowable operation range, the operation status signal will be determined as a sensor value error.

In the case when the operation status signal is determined as being valid, the determination section 12 does not cause any action directed to the control section 10I. In the case when the operation status signal is determined as being invalid, the determination section 12 reads out from the memory section 15 the previous data on the angle having been acquired just before that determination process and determined as valid. Then the determination section 12 outputs the read out data as a replacement signal to the control section 10I, the replacement signal being a signal for replacing the sensor value (determined as invalid) of the sensor 11I with the previous sensor value having been determined as valid. Thus, the determination section 12 has a replacement section 16 for outputting the replacement signal.

Meanwhile, in the case when the memory section 15 is to store the sensor values in time series, it is possible to arrange such that the memory section 15 also stores the determination results as obtained by the determination section 12. Moreover, in storing the sensor value, it can be arranged such that the sensor value is stored as being associated with the time of storage.

In this way, according to the present embodiment, in the case when the operation status signal is determined as deviating from the allowable operation range and thus as being abnormal or an error, the previous sensor value having been determined as valid just before the error is determined, is used as a predetermined condition considered appropriate, in controlling the active mechanism 7I so as to continue operating.

In the case when the operation status signal is determined as being valid (by the determination section 12), the control section 10I uses the sensor value from the sensor 11I as a control signal for controlling the driving signal. On the other hand, in the case when the operation status signal is determined as being abnormal, the control section 10I uses the replacement signal outputted from the determination section 12 as the control signal (instead of the sensor value of the sensor 11I).

In FIG. 1, although the setting section 14 and the determination section 12 are shown in different blocks, it is possible to configure the determination section 12 as including the setting section 14.

The configuration of the manipulator is not limited to the block configuration as shown in FIG. 1. In the case when the determination section 12 determines that the operation status signal is deviating from the allowable operation range and thus is abnormal or an error, it is possible to arrange such that the replacement section 16, for example, uses the previous sensor value having been determined as valid just before the error is determined, in order to generate a driving signal for a time after the determination.

That is, in the case when the operation status signal is determined as deviating from the allowable operation range, it is possible to arrange such that the replacement section 16 uses the previous sensor value in generating a driving signal for a time after the determination.

As will be described in terms of an operation example later on, the determination section 12 not only determines whether the data on the angle as acquired directly from the sensor 11I is within the allowable operation range but also determines whether data on angular velocity, angular acceleration, etc. are within the allowable operation ranges. In this way, it is arranged such that the determination section 12 is capable of performing determinations with higher precision.

For such purpose, the determination section 12, has a calculation section 17 which calculates, based on the data on angle as acquired by the sensor 11I, an angular velocity on the basis of time dependent change in the angle in a short period of time, and further calculates, based on the information on the angular velocity as calculated, an angular acceleration based on time dependent change in the angular velocity in a short period of time. Furthermore, the setting section 14 sets the allowable operation range not only with respect to the angle but also with respect to the angular velocity and the angular acceleration.

As will be described in more detail with reference to FIG. 3A, etc., practically, the angle, which is taken as the operation status signal, at each time point in the passage of time is monitored and determined whether it is within the allowable operation range. Therefore, change in the angle in a short period of time will be determined whether it is within an allowable operation range, or in other words, within an allowable operation change range, for that period of time.

In the endoscope treatment system 1 according to the present embodiment, a manipulator 20, as shown in FIG. 1, includes the endoscope 2, the treatment instrument 3, the control device 8, and the instruction input devices 9A and 9B. In a configuration example shown in FIG. 8, the display processor 5 and the display device 6 are also included in the manipulator as parts that form a display mechanism of the manipulator.

The display processor 5 shown in FIG. 1 controls the amount of illuminating light from the light source device 4 based on luminance information indicated by a video signal, for instance.

Figure 2:
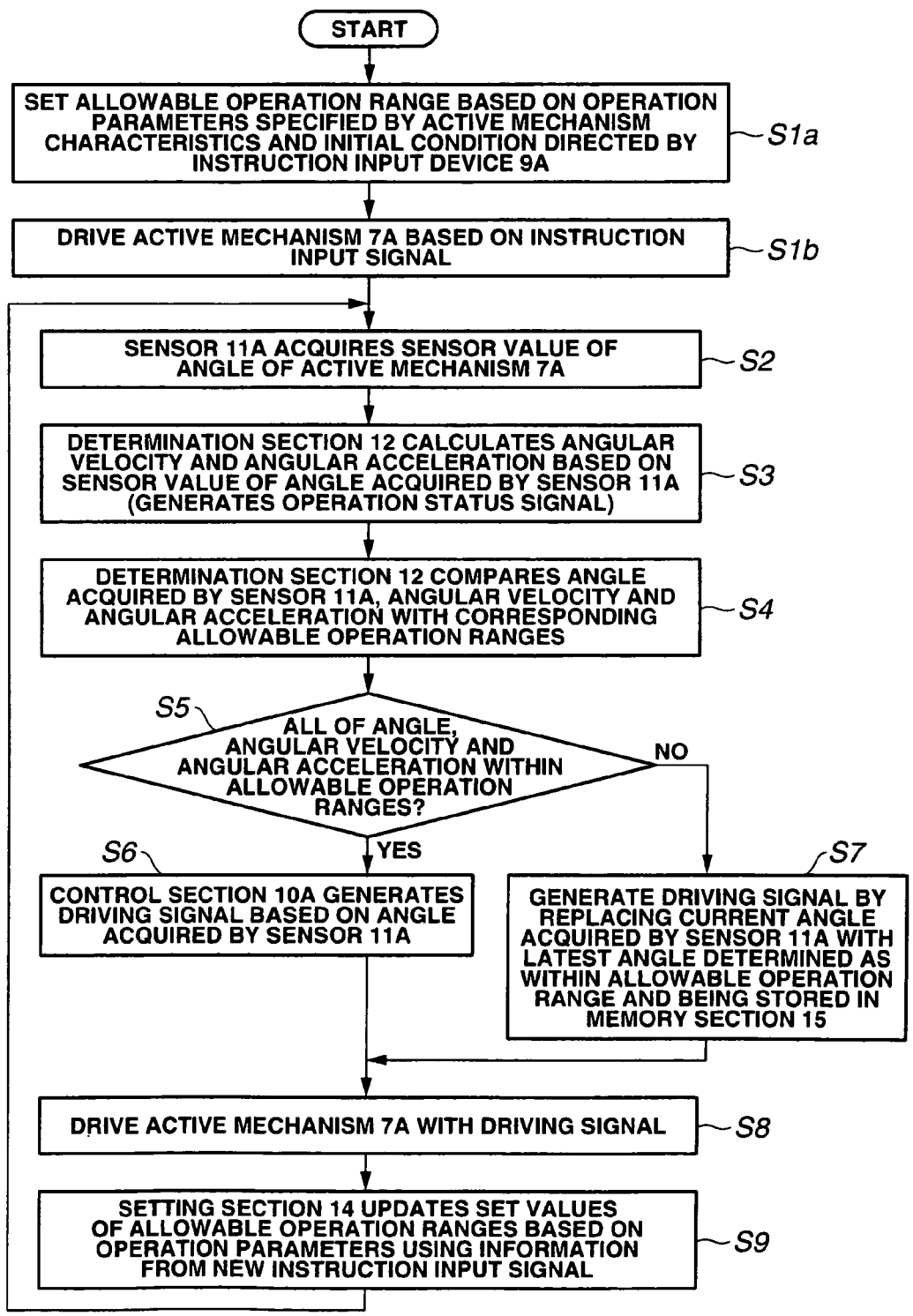
FIG. 2 is a flow chart showing contents of processes in an operation of the endoscope treatment system that includes the first embodiment of the present invention.

Next, an operation according to the present embodiment will be described with reference to a flow chart of FIG. 2. FIG. 2 shows procedures in a method of controlling the manipulator according to the present embodiment. In the following, an operation in a case where the active mechanism 7A of the endoscope 2 is actively driven will be described, for example.

As power is supplied to the endoscope treatment system 1 shown in FIG. 1, the control device 8, etc. start operating.

Then at step S1a indicated in FIG. 2, the setting section 14 as arranged inside the control device 8 sets an allowable operation range as being a predetermined range where the active mechanism 7A is physically operable, based on operation parameters (of the active mechanism 7A) that can be specified by the active mechanism characteristics (being stored in the active mechanism characteristic storage section 13) and an initial condition (which is to be ignored when it is undecided, and will be considered in a next loop) directed by the instruction input device 9A. By this setting, allowable operation ranges with respect to the angle, angular velocity and angular acceleration are set for the driving of the active mechanism 7A.

Then at step S1b following step S1a, the control section 10A drives the active mechanism 7A based on the instruction input signal from the instruction input device 9A. Then at step S2, the sensor 11A acquires a sensor value with respect to the driven angle as a measured value.

At step S3, the determination section 12 calculates the angular velocity and the angular acceleration based on the sensor values with respect to the angle as acquired by the sensor 11A. That is, the angle, the angular velocity and the angular acceleration, to be regarded as an operation status signal, are calculated by the determination section 12. With respect to a case shown in FIG. 3A, which will be described in more detail later on, angular change in a short period of time as the angle will be detected.

Then at a subsequent step S4, the determination section 12 compares the calculated values of the angle, the angular velocity and the angular acceleration, regarded as the operation status signal, with the allowable operation ranges with respect to the angle, the angular velocity and the angular acceleration, which have been set by the setting section 14, in order to determine whether each of the values is within the corresponding allowable operation range.

Then at step S5, it is determined whether all the values of the angle, the angular velocity and the angular acceleration are within the allowable operation ranges. In other words, the validity of these values is determined. When it is determined that all the values of the angle, the angular velocity and the angular acceleration are within the allowable operation ranges, i.e. when it is determined that the values are valid, the control section 10A, at step S6, generates a driving signal for a next time based on the value of the angle as acquired by the sensor 11A.

Then at step S8, the driving signal is supplied to the active mechanism 7A, whereby the active mechanism 7A is driven.

Meanwhile, if it is determined at step S5 that at least one of the values of the angle, the angular velocity and the angular acceleration is not within the allowable operation range, i.e. when it is determined that the value is invalid, the process of step S7 is carried out.

In this case, the determination section 12 reads out from the memory section 15 the latest previous data on the angle stored in the memory section 15 (i.e. the previous data on the angle acquired just before the time where the value is determined invalid), having been determined as being within the allowable operation range, and replaces the value of the angle as acquired by the sensor 11A with the read out data on the angle in order to generate a driving signal. For a case in that the previous data on the angle acquired by the sensor 11A has not been stored in the memory section 15 with respect to the initial processing loop, it is being set such that an initial value (e.g. 0°) should be used. Then the operation proceeds to a subsequent step S8.

After step S8, using information from a new instruction input signal, the setting section 14 updates the set values of the allowable operation ranges having been set based on the previous operation parameters. Then, the operation goes back to step S2. In this way, when driving conditions of the active mechanism 7A are changed due to the change in the operation parameters of the active mechanism 7A, the allowable operation ranges are updated complying with the change.

Then, the determination section 12 determines whether the operation status signal with respect the angle, or the like, as acquired by the sensor 11A is within the updated allowable operation range. When the determination result indicates that the operation status signal is valid, the control section 10A generates a driving signal based on the value of the angle as acquired by the sensor 11A. Meanwhile, if the determination result indicates that the operation status signal is invalid, the control section 10A generates a driving signal based on the latest previous data on the angle stored in the memory section 15, having been determined as valid, the latest previous data on the angle being obtained from the memory section 15 through the replacement section 16.

By executing such drive control, if the sensor value acquired by the sensor 11A or other values of the operation status signal derived based on that sensor value come to invalid states while an operator is performing some medical treatment such as an endoscopic examination or the like using the active mechanism 7A of the endoscope 2, the drive control on the active mechanism 7A can be continued. Therefore, the medical treatment will not be forced to abnormal termination. Next, a specific example of the operation of the active mechanism 7A in terms of the processes shown in FIG. 2 will be described with reference to FIG. 3A to FIG. 5A.

Figure 3A:
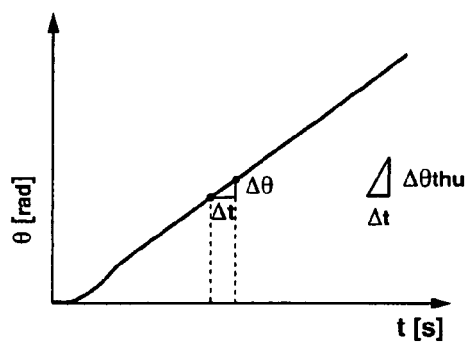
FIG. 3A and FIG. 3B are diagrams showing examples of an angle of a motor configuring an active mechanism as the motor is rotated by a constant output, and a sensor value of angle acquired by a sensor.
Figure 3B:
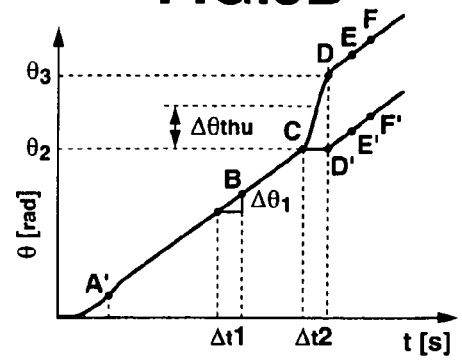
Figure 4A:
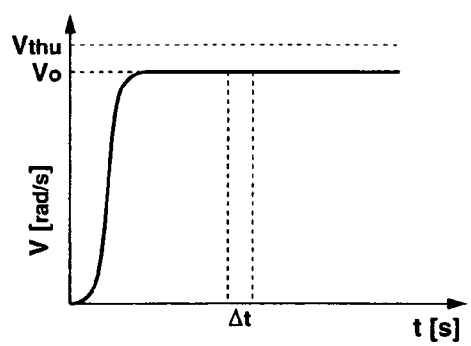
FIG. 4A and FIG. 4B are diagrams showing examples of an angular velocity of the motor configuring the active mechanism as the motor is rotated by the constant output, and an angular velocity calculated based on the sensor value acquired by the sensor.
Figure 4B:
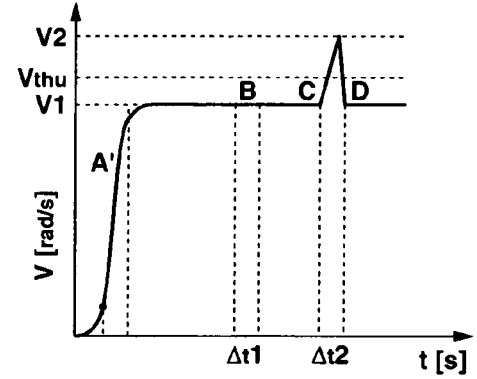
Figure 5A:
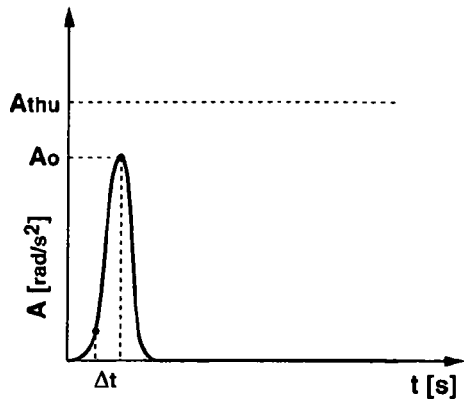
FIG. 5A and FIG. 5B are diagrams showing examples of an angular acceleration of the motor configuring the active mechanism as the motor is rotated by the constant output, and an angular acceleration calculated based the sensor value acquired by the sensor.
Figure 5B:
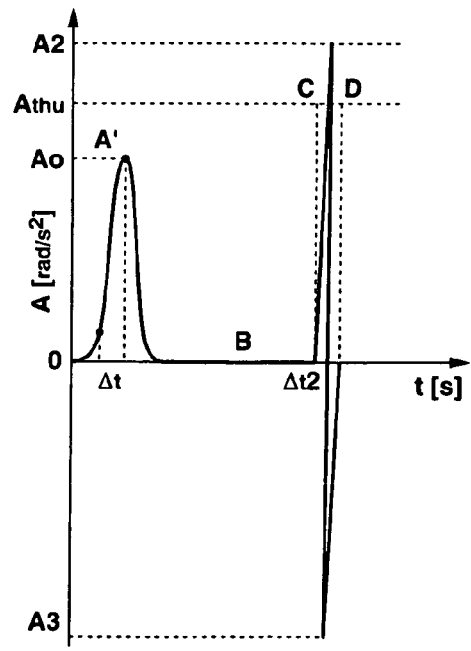

FIG. 3A, FIG. 4A and FIG. 5A are graphs showing time dependent changes in angle θ, angular velocity V and angular acceleration A when the active mechanism 7A of the endoscope 2 is actually driven with a constant rated output. FIG. 3B, FIG. 4B and FIG. 5B are graphs showing changes in angle θ, angular velocity V and angular acceleration A calculated by the calculation section 17 inside the determination section 12 based on sensor values (i.e. raw data equivalent to angles) as acquired by the sensor 11A.

FIG. 3B shows an example of a case where a sensor value error or a sensor value acquisition error has occurred. In the present embodiment, a sensor value error can be defined as a counter error (counting error) with respect to an output pulse of an encoder, for example, which could occur due to a waveform of the encoder being disturbed by noise, etc.

As shown in FIG. 3A, since the active mechanism 7A is driven with a constant rated output, the number of rotations with the motor that configures the active mechanism 7A becomes constant, except at a starting time, whereby the angle becomes larger by the same degrees with respect to time. That is, the angular change Δθ per short unit time Δt becomes constant.

In a practical sense, there may be a case in which the number of rotations is rendered unstable due to a load, such as disturbance, placed on the endoscope 2. However, the case of FIG. 3A is supposed to be an example where influence of such load on the value of the angular change Δθ is small enough.

As shown in FIG. 4A and FIG. 5A, the angular velocity V and the angular acceleration A change with time. Specifically, as shown in FIG. 4A, the angular velocity V becomes a constant angular velocity $V_0$ except in a time around the starting time.

As shown in FIG. 5A, the angular acceleration A changes in a peaking manner (with a peak value being "$A_0$") only in a time around the starting time, and the value thereof becomes 0 from after that time around the starting time.

In the case where the active mechanism 7A of the endoscope 2 is driven with the operation parameter as being the constant rated output condition shown in FIG. 3A, the setting section 14 sets the allowable operation ranges (usually, such allowable operation range is a range with a lower limit and a higher limit where values under normal status are included) with respect to the angle θ or the angular change (angular inclination) Δθ, the angular velocity V and the angular acceleration A with which the motor configuring the active mechanism 7A becomes physically operable.

In FIG. 3A, the allowable operation range is shown in terms of the angular change Δθ, but when the allowable operation range is to be shown in terms of the angle θ, it will change approximately linearly with the passage of time.

For example, in terms of the angular change Δθ, the allowable operation range will be "Δθthl<Δθthu", whereas the allowable operation ranges in terms of the angular velocity V and the angular acceleration A will be "Vthl<Vthu" and "Athl<Athu", respectively.

In a normal (valid) status, the allowable operation ranges will be "Δθthl<Δθ<Δθthu", "Vthl<V<Vthu" and "Athl<A<Athu", respectively.

In this example, although the allowable operation ranges in terms of the angular velocity V and the angular acceleration A are shown as constant values, there may be cases where it is better (easy to determine) if the allowable operation ranges are set in terms of angular velocity change ΔV and angular acceleration change ΔA, depending on the operation parameters.

In FIG. 3A to FIG. 5B, the graphs are simplified, and only the values Δθthu, Vthu, and Athu on the upper limit sides are shown. Moreover, for the sake of simplicity, the examples represented by the graphs show the values Δθthu, Vthu, and Athu on the upper limit sides of the allowable operation ranges as constant values.

Meanwhile, the sensor 11A detects the angle of the active mechanism 7A (motor) every short unit time Δt. The sensor value acquired by the sensor 11A is inputted to the determination section 12, where the calculation section 17 inside the determination section 12 calculates the angular change Δθ in the unit time Δt based on the sensor value; the angular velocity V based on time dependent change in the angle; and the angular acceleration A based on time dependent change in the angular velocity.

Here, since the angular change Δθ is calculated almost uniquely from the sensor value, it is possible to interpret that the calculation section 17 calculates the angular velocity V (or the angular velocity change) and the angular acceleration A (or the angular acceleration change) based on the angle θ or the angular change (the information on the angle θ or the angular change).

In FIG. 3B, FIG. 4B and FIG. 5B, representative points in the passage of time t are shown as A', B, C and D. It is assumed that from point A' around the starting point to point B after the angular velocity becomes constant (at a value V1), and further up to point C after that, the sensor value of the sensor 11A is normal, whereas an error occurs in the sensor value between point C and point D.

Points E and F in FIG. 3B are drawn for the purpose of explaining the processes according to the present embodiment in the case when the error occurs between points C and D, the processes supposed to be performed after the error has occurred between points C and D. As will be described below, in the case when the error occurs, the active mechanism 7A will be controlled substantially using sensor values such as those at point D' (i.e. a sensor value at point C), point E' and point F'.

In FIG. 3B, the unit time Δt around point B, for example, is shown as Δt1, and a value of change in the angle detected by the sensor 11A in that case is shown as Δθ1.

As shown in FIG. 5B, the angular acceleration A takes a peaking form (with a peak value being "A1") around the starting point A', and maintained at 0 until just before point C. Then, in the unit time Δt (i.e. Δt2) between point C and point D, the angular acceleration A greatly changes due to disturbance by noise, for example.

In response to such change, the angular velocity V and the angular acceleration A as calculated from the sensor value of the sensor 11A change in ways shown in FIG. 4B and FIG. 5B.

For example, the angular velocity V changes in a form of a precipitous triangular waveform, where it becomes a peak value V2 at a time just before point D from a value V1 at point C and then precipitously returns to V1. The angular acceleration A exhibits a characteristic in that it rises more precipitously up to a peak value A2, after which it drops precipitously down to a negative peak value A3 and then precipitously rises again to become 0.

In FIG. 3B, FIG. 4B and FIG. 5B, the angular change Δθ (i.e. θ3−θ2), the angular velocity V and the angular acceleration A, as calculated based on the sensor value between point C and point D, exceed Δθthu, Vthu and Athu, which are their allowable operation ranges. Therefore, the determination section 12 determines that the angular change Δθ, the angular velocity V and the angular acceleration A in this case are deviating from the allowable operation ranges, and thus are errors.

In the examples shown by FIG. 3B, FIG. 4B and FIG. 5B, the angular change Δθ, the angular velocity V and the angular acceleration A, as calculated based on the sensor value between point C and point D, exceed Δθthu, Vthu and Athu, respectively. However, even with only one of the values being found deviating from the allowable operation range, an error will be determined. In such case, the following controlling process will be carried out.

The determination section 12 determines that an angle θ3 as being a sensor value at point D is an error. Then, the determination section 12 does not use that value but takes an angle θ2, as being a sensor value acquired at a time just before Δt2 with which an error was not determined, to be a sensor value of a replacement signal, and transmits that replacement signal to the control section 10A.

The control section 10A controls to generate a driving signal using this replacement signal. Accordingly, as shown in FIG. 3B, in stead of the sensor value at point D, the sensor value at point C, i.e. a sensor value at point D', is used in controlling the active mechanism 7A.

Moreover, the determination section 12 stores information on the sensor value as being found to be an error in the memory section 15, for instance. Specifically, the determination section 12 stores a value "θ3−θ2", for example, as a correction value W in the memory section 15. Then, the determination section 12 corrects the sensor value (of the sensor 11A) acquired from after point D with the correction value W. Thus, the determination section 12 functions as a correction section that corrects a sensor value in a case when an error occurs. Specifically, a sensor value acquired at point E after the unit time Δt from point D will include the sensor value with which the error has occurred unless corrected. Therefore, a sensor value at point E' as corrected with the correction value W is used (in this case, a value derived by subtracting the correction value W from the sensor value). Likewise, for point F after point E, a sensor value at point F' as corrected with the correction value W will be used as a corresponding sensor value.

Meanwhile, it is possible to reconfigure the sensor 11A itself so that the sensor 11A will be able to output a value with a correct sensor value. In such case, however, the sensor 11A needs to be reset whereby the operation is required to be stopped (and restarted) in the middle. To cope with this, by the correction with the above-mentioned correction value, it is possible to allow the operation to continue smoothly without having to stop in the middle.

FIG. 6 shows processes taken in the above-described case in which the error occurs, that is, FIG. 6 shows the content of the process at step S7 in FIG. 2 in more detail.

In the examples shown by FIG. 3A to FIG. 5B, or in the case when at least one of the angle indicated by the sensor value or the angular change $\Delta\theta$, the angular velocity V, and the angular acceleration A is found to be deviating from the allowable operation range, i.e. in the case when the determination section 12 determines that an error has occurred, at step S5 in FIG. 2, the determination section 12, at step S11 indicated in FIG. 6, reads out from the memory section 15 the sensor value (angle $\theta 2$ shown in FIG. 3B) having been acquired just before the occurrence of the error.

Then at step S12, the determination section 12 outputs the sensor value $\theta 2$ to the control section 10A as a replacement signal that replaces the sensor value $\theta 3$ at the occurrence of the error.

Then at step S13, the control section 10A replaces the sensor value $\theta 3$ at the occurrence of the error with the replacement signal and generates a driving signal.

Meanwhile, at step S14, the determination section 12 takes a shift amount, for example, between the sensor value $\theta 3$ at the occurrence of the error and the sensor value $\theta 2$ acquired at the time just before the occurrence of the error to generate a correction value W.

Then at step S15, the determination section 12 uses the correction value W to correct the sensor value acquired after the sensor value $\theta 3$ at the occurrence of the error. Moreover, the determination section 12 transmits the correction value W to the control section 10A, whereby the control section 10A uses the correction value W to correct the sensor value acquired after the sensor value $\theta 3$ with which the error has occurred, and generates a driving signal.

In this case, with a configuration where the sensor value of the sensor 11A is outputted to the control section 10A through the determination section 12, the correction process using the correction value W at the side of the control section 10A is not necessary.

By such drive control, as shown in FIG. 3B for instance, even when an error occurs in the sensor value during the operation of the active mechanism 7A, the active mechanism 7A can be controlled continuously with a response delay corresponding to a period of time $\Delta t2$ in which the error occurred. Therefore, the operation of the active mechanism 7A does not need to be stopped and terminated (i.e. forced to abnormal termination) due to the occurrence of the error.

Accordingly, even when an error occurs, a user, such as an operator, will be able to continue the operation by the active mechanism 7A of the endoscope 2 without having the operation forced to abnormal termination due to the occurrence of the error. Thus, operability can be improved to a considerable extent.

Although the description of the operation which has been given referring to FIG. 3A to FIG. 6 is about the case of the endoscope 2, it can also be applied to a case of the active mechanism 7B of the treatment instrument 3.

Figure 7:
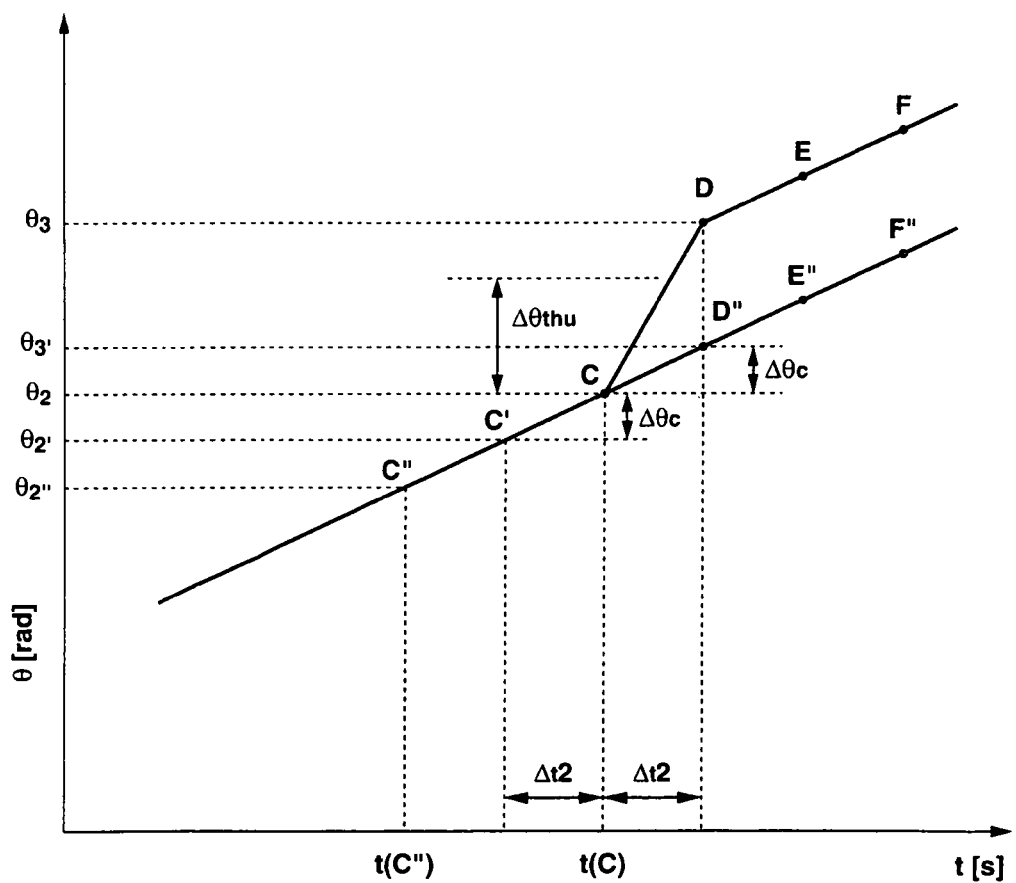
FIG. 7 is an explanatory diagram of an operation, according to a variant example, in a case of error being determined.

FIG. 7 shows a content of a process (error process) at an occurrence of an error according to a variant example. The above-described error process is equivalent to a control (control means or control method), with which, in a case where an error occurs (occurrence of an error is determined), the status of the sensor value can be rendered substantially the same as before the occurrence of the error, and thus the driving status (operation status) of the active mechanism 7A can be maintained.

On the other hand, in the variant example as will be described below, a driving control (process) at an occurrence of an error is controlled to be carried out in a manner similar to that before the occurrence of the error.

As a specific example for such case, as shown in FIG. 7, for instance, an angular change between an angle $\theta 2$ of a sensor value at point C just before the occurrence of the error and an angle $\theta 2'$ of a sensor value at point C' a unit time $\Delta t2$ before point C is considered $\Delta\theta c$.

In this case, an angle $\Delta 3$ of a sensor value at point D at the occurrence of the error is not used, while a value that can be derived by adding the angle $\Delta 2$ of the sensor value at point C and the angular change $\Delta\theta c$ is rendered a sensor value $\theta 3'$ or a replacement signal.

In other words, in the occurrence of the error, the control section 10A (or the replacement section 16) generates a driving signal in the following manner.

In the occurrence of the error, the control section 10A does not use the current sensor value, but replaces that sensor value with a previous error-free sensor value acquired just before. Along with that, the control section 10A generates a driving signal to be used from the time after the occurrence of the error by adding an amount of change, which can be estimated based on a value of the previous sensor value (an angular velocity if the sensor value is of an angle) as it comes up to the point where the error has occurred, to the previous sensor value.

Moreover, the determination section 12, for example, stores the value of "$\theta 3-\theta 3'$" in the memory section 15, etc. as a correction value W, and uses that correction value W to correct the sensor values acquired after the point where the error has occurred.

In such case, the sensor values at points D, E and F shown in FIG. 3B will be corrected such that they will become as sensor values at points D", E" and F"' shown in FIG. 7.

By adopting the error process of this variant example, in such case where the amount of angular change per unit time is small, it is possible to carry out the control while restraining possible decrease in responsiveness.

In addition, as a second variant example, it is possible to use a temporal average value with respect to the angular change before the occurrence of the error, instead of the angular change $\Delta\theta c$.

Specifically, an average angular change $<\Delta\theta c>(=(\theta 2-\theta 2")/(t(c)-t(c")))$ in a period of time from point C", which is further before point C', where a sensor value of an angle $\theta 2"$ was acquired up to point C where the sensor value of the angle $\theta 2$ was acquired can be used instead of the angular change $\Delta\theta c$. Here, t(c) and t(c") indicate times at point C and point C", respectively.

It is possible to arrange such that a user can select from among the error process according to the first embodiment and the error processes according to the variant examples.

Figure 8:
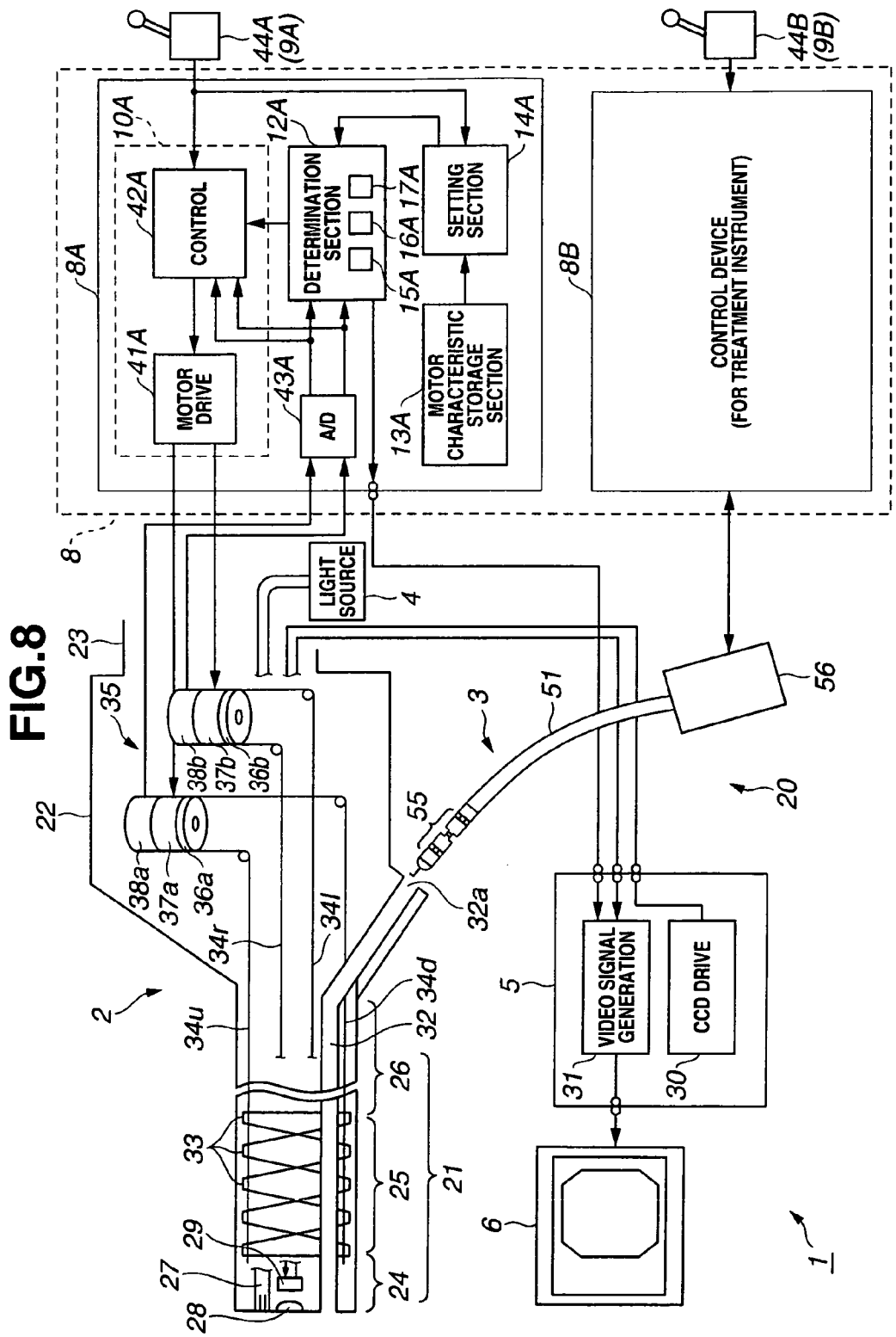
FIG. 8 is a diagram showing a specific configuration example of peripheral equipment as well as an endoscope shown in FIG. 1.

Next, with reference to FIG. 8, a specific configuration example of the endoscope treatment system 1 shown in FIG.

1 will be described. FIG. 8 shows specific configuration examples of the endoscope 2 and so forth.

The endoscope 2 has an elongated insertion section 21 to be inserted into a body, an operation section 22 arranged at a posterior end of the insertion section 21 and a universal cable 23 extending from the operation section 22. An end portion of the universal cable 23 is connected to the light source device 4, the display processor 5 and the control device 8 through connectors, which are not shown, in detachable manners.

The insertion section 21 has a distal end section 24 arranged at a distal end thereof, a bendable bending section 25 arranged at a posterior end of the distal end section 24, and a flexible section 26 which exhibit flexibility in a length between a posterior end of the bending section 25 and an anterior end of the operation section 22. The bending section 25 is actively bend-driven by a motor unit 35 arranged inside the operation section 22.

The distal end section 24 has an illumination window and an observation window arranged thereat. The illumination window has a distal end surface of a light guide 27 attached thereto. This light guide 27 has a posterior end thereof connected to the light source device 4 through the insertion section 21, the operation section 22 and the universal cable 23, and will transmit illuminating light from the light source device 4 in order to emit the illuminating light from its distal end surface.

In stead of the light guide 27, a light-emitting diode (to be referred to as LED) may be arranged at the distal end section 24 to use the light emitted from the LED as the illuminating light.

A subject, such as an affected part inside a body, as being irradiated with the illuminating light emitted through the illumination window will be formed into an optical image by an objective lens 28 attached to the observation window. A charge-coupled device (to be referred to as CCD) 29, for example, is arranged at an image forming position, and photoelectric conversion is carried out by this CCD 29.

The CCD 29 is connected to the display processor 5 through a signal line which is being inserted inside the insertion section 21, etc. The CCD 29 will output a photoelectric-converted image pickup signal in response to a CCD driving signal supplied from a CCD drive circuit 30 arranged inside the display processor 5.

This image pickup signal will be inputted to a video signal generation circuit 31 arranged inside the display processor 5 where it will be converted into a video signal. Then the video signal will be inputted to the display device 6, whereby the optical image having been formed on an image-pickup surface of the CCD 29 will be displayed on a display surface of the display device 6 as an endoscope image.

A treatment instrument insertion opening (to be referred to as insertion opening) 32a is arranged around the posterior end of the insertion section 21, i.e. around the anterior end of the operation section 22. The insertion opening 32a is in communication with a treatment instrument channel (to be referred to as channel) 32 which is formed in a longitudinal direction of the insertion section 21.

The treatment instrument 3, from the distal end side thereof, can be inserted into the treatment instrument channel 32 through the treatment instrument insertion opening 32a. Then the distal end of the treatment instrument 3 can be projected from a distal end opening of the channel 32, whereby the treatment instrument 3 will be able to perform a treatment such as resecting a lesioned part, or the like, for instance.

The bending section 25 has a plurality of circular bending pieces or joint pieces (to be referred to as joints) 33, 33, ..., 33 being connected through pivoted members such as rivets, in a turnable manner. The pivoted members can be arranged, for instance, at upper and lower positions and at right and left positions.

For the purpose of bend-driving the plurality of joints 33, 33, ..., 33 that configure the bending section 25, up and down bending wires 34u and 34d, and left and right bending wires 34l and 34r are inserted inside the insertion section 21. A distal end of each wire 34j (=u, d, l, r) is fixed to the joint 33 at the farthest end or to the distal end section 24 to which the joint 33 at the farthest end is connected.

Posterior ends of the paired wires 34u and 34d, and posterior ends of the paired wires 34l and 34r are winded, for example, around an up-and-down bending pulley 36a and a right-and-left bending pulley 36b, respectively. The up-and-down bending pulley 36a and the right-and-left bending pulley 36b are arranged inside the motor unit 35 which configures the active mechanism 7A that actively drives the bending section 25, while the motor unit 35 is being arranged inside the operation section 22.

With this configuration, one of the wires 34u and 34d can be pulled while the other can be relaxed, for example, by causing the pulley 36a to turn (rotate), whereby the joints 33, 33, ..., 33 of the bending section 25 can be bend-driven toward the pulled wire.

The pulleys 36a and 36b are connected to rotation axes of an up-and-down bending motor 37a and a right-and-left bending motor 37b, respectively, through gears, which are not shown. Rotation angles of the respective motors 37a and 37b (or rotation angles of the respective pulleys 36a and 36b) that configure a rotary drive section will be detected by respective rotary encoders (to be referred to as encoders) 38a and 38b that configure the sensor 11A.

The motors 37a and 37b are rotary driven with driving signals supplied from a motor drive circuit 41A arranged inside the control section 10A that configures a control device 8A (for endoscope) inside the control device 8, whereby the wires 34u, 34d, 34l and 34r are pulled/relaxed to actively drive the bending section 25.

Encoder output signals (as sensor values) outputted from the encoders 38a and 38b will be inputted to a control circuit 42A inside the control section 10A through an A/D conversion circuit 43A as digital operation status signals (specifically, detected angles). These digital operation status signals will be inputted to a determination section 12A as well.

A signal (as an instruction input signal) with respect to bending direction and angle, corresponding to an instruction input operation by the user, will also be inputted to the control circuit 42A through a joystick 44A, which is a specific example of the instruction input device 9A.

The control circuit 42A, in a usual (normal) case, takes a signal of a difference value derived by subtracting the encoder output signal from the instruction input signal as a new instruction input signal, and outputs this new instruction input signal to the motor drive circuit 41A. Then the motor drive circuit 41A will output driving signals corresponding to such instruction input signal to the motors 37a and 37b.

Meanwhile, in such event that the encoder output signal is determined as invalid through a determination process by the determination section 12A, as will be described bellow, the motor drive circuit 41 takes in a replacement signal from a replacement section 16A inside the determination section 12A to use the replacement signal as a new instruction input signal, and outputs that instruction input signal to the motor drive circuit 41A. That is, in an unusual (abnormal) case, generation of the driving signals by the motor drive circuit 41A is controlled by the replacement signal from the determination section 12A.

Therefore, the encoder output signals outputted from the encoders 38a and 38b will also be inputted to the determination section 12A through the A/D conversion circuit 43. These encoder output signals will be stored in a memory section 15A inside the determination section 12A.

Moreover, in the present embodiment, a motor characteristic storage section 13A where motor characteristics of the motors 37a and 37b are stored is provided. Data on the motor characteristics will be inputted to a setting section 14A.

The setting section 14A sets allowable operation ranges based on the motor characteristics and the instruction input signal (or an updated instruction input signal generated by the control circuit 42A).

Furthermore, the determination section 12A, for example, detects (acquires) information on an angle directly from the encoder output signal, while the determination section 12A calculates by a calculation section 17A therein an angular velocity based on time dependent change in the angle, and an angular acceleration based on time dependent change in the angular velocity.

Then based on the information on the allowable operation ranges as being set by the setting section 14A, the determination section 12A performs validity determination to determine whether the angle (or the angular change), the angular velocity and the angular acceleration, regarded as the operation status signal, are within or deviating from the allowable operation ranges.

As described above, when the operation status signal is found to be within the allowable operation range, the control section 10A that configures a driving signal generation section uses the encoder output signal, i.e. information on the angle, to generate a new driving signal.

On the other hand, when the operation status signal is determined as deviating from the allowable operation range, the control section 10A reads out from the memory section 15A, where the encoder output signals are stored in time series, the latest previous signal (i.e. a signal at a time just before the operation status signal has been determined as being deviating from the allowable operation range) corresponding to the encoder output signal with which the operation status signal has been determined as being within the allowable operation range.

Then the determination section 12A outputs the read out signal to the control circuit 42A as a replacement signal. The control circuit 42A takes the replacement signal as the operation status signal of the usual case to generate a subsequent driving signal.

Thus, in the present embodiment, the detection signals of the encoders 38a and 38b functioning as sensors and the signals indicating the time-dependent changes in the values of the detection signals are monitored. Then in the case when the monitored signals are determined as being within the allowable operation ranges, it is controlled such that the driving signal is generated based on the detection signals of the encoders 38a and 38b. On the other hand, in the case when the monitored signals are determined as being abnormal because of deviating from the allowable operation ranges, it is controlled such that the driving signal is generated based on the latest previous detection signals of the encoders 38a and 38b having been determined as normal.

In the case when the monitored signals are determined as abnormal, and it comes to the state that the driving signal needs to be controlled based on the prior detection signals of the encoders 38a and 38b which have been determined as normal, the determination section 12A outputs a signal for informing that abnormal status directed to the video signal generation circuit 31 of the display processor 5. Thereby, displays indicating that abnormal status has been determined, and that the driving operation is proceeding based on the latest detection signals of the encoders 38a and 38b will be put on the display surface of the display device 6. Moreover, it is also possible to arrange such that information on the determination result in the normal status can be indicated, in addition to indicating the state of determination result in the abnormal status.

In such a case where an operator, such as a surgeon, is in the middle of performing an endoscope examination, bending control on the bending section 25 can be executed continuously.

By executing such control, even in a case when the detection signals of the encoders 38a and 38b are found deviating from the allowable operation ranges due to noise, for example, the operation can be continued based on the detection signals of the encoders 38a and 38b acquired at the time just before the occurrence of the noise.

In other words, in a case when the detection signals of the encoders 38a and 38b are found deviating from the allowable operation ranges due to noise, for example, the current detection signals of the encoders 38a and 38b are not used in controlling the drive section, but the operation is made to continue based on the detection signals of the encoders 38a and 38b in the normal case acquired at the time just before the occurrence of the noise.

Such condition in the case where the detection signals of the encoders 38a and 38b are found deviating from the allowable operation ranges due to noise is almost equivalent to a condition in which the control status or the operation status where the normal status at the time just before the deviance has found is maintained can be kept, with only a temporal response rate decrease in a short period of time.

Then, after that, when a normal status is determined by the determination section 12, the drive section will be controlled by the detection signals of the encoders 38a and 38b again. In this way, in the case when the detection signals of the sensors are found to be deviating from the allowable operation ranges due to noise, it is possible to control to maintain the control status at a nearly appropriate state and allow the bend-driving of the bending section 25 to be continued.

Figure 9:
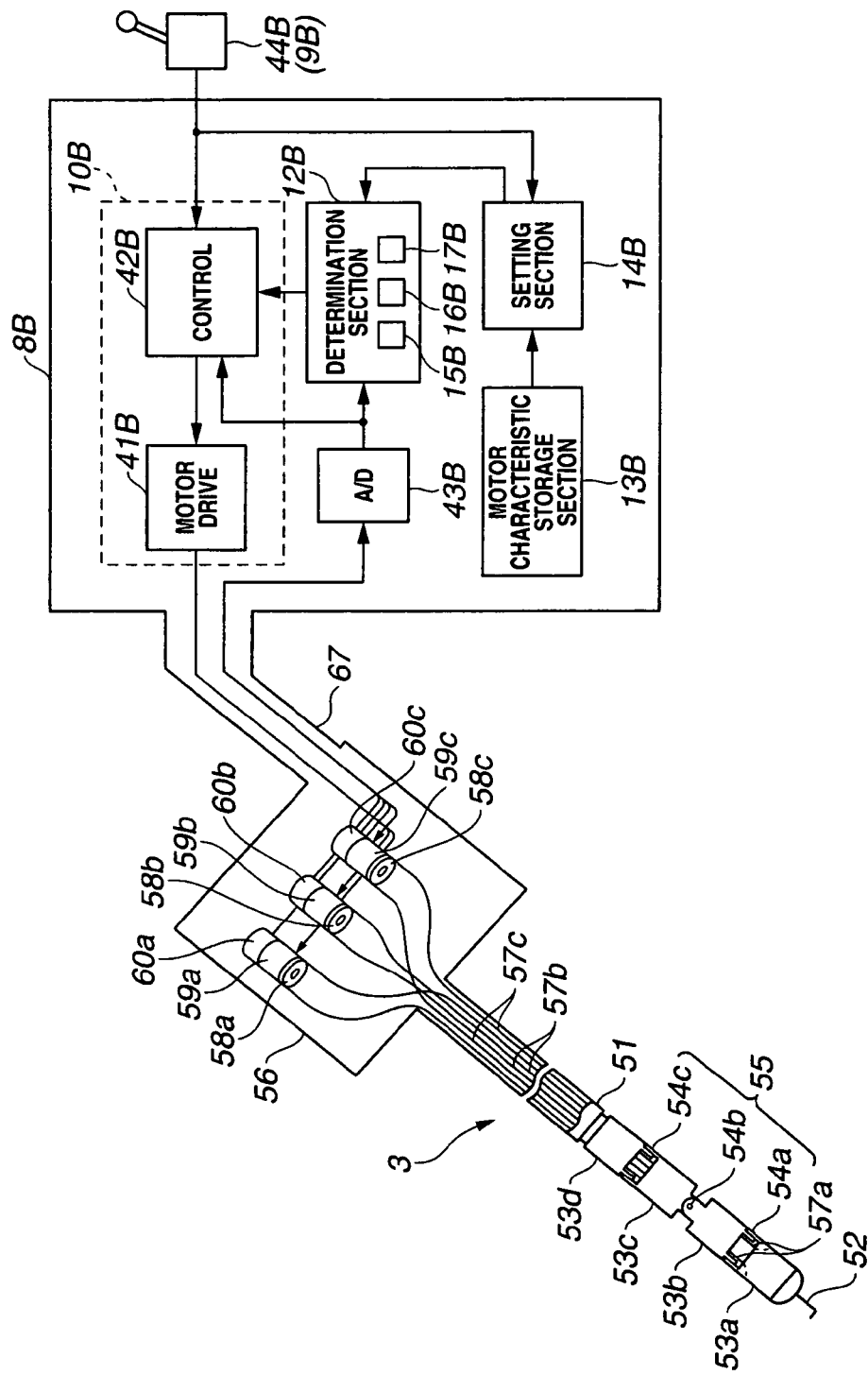
FIG. 9 is a diagram showing specific configuration examples of a treatment instrument shown in FIG. 1 and a control device of the treatment instrument.

On the other hand, FIG. 9 shows a configuration of the treatment instrument 3 to be inserted into the channel 32 of the endoscope 2. As shown in FIG. 9, the treatment instrument 3 has an elongated axis section 51 (as a treatment instrument insertion section), for instance, which can be inserted into the channel 32. A treatment section 52, which is used in performing a treatment such as resection, is formed at a distal end of this axis section 51.

At a posterior end of the treatment section 52, a bending section (flexion section) 55 is formed. The bending section 55 has a plurality of joints 53a, 53b, ..., 53d being connected through pivoted sections 54a, 54b and 54c in a turnable manner, the pivoted sections 54a, 54b and 54c being arranged adjacent to and in a longitudinal direction of the joints 53a, 53b, ..., 53d.

At a posterior end of the axis section 51, a motor box 56 as being a drive section for electrically driving the bending section 55 is arranged. A cable 67 which extends from this motor box 56 is connected to a control device 8B (for treatment instrument).

In FIG. 9, for example, the joint 53a at the farthest end to which a proximal end of the treatment section 52 is fixed is rotatably connected to the adjacent joint 53b through the pivoted section 54a, in a vertical direction with respect to the paper surface, for example.

Wires 57a and 57a which transmit driving force for rotational movement have distal ends thereof fixed to a direct front position of the pivoted section 54a at the joint 53a. These wires 57a and 57a are being inserted inside the joints 53b, ..., 53d, and winded around a pulley 58a arranged inside the motor box 56.

This pulley 58a is connected to a rotation axis of a motor 59a with which rotation the pulley 58a can be rotated. An encoder 60a which functions as a sensor for detecting (acquiring) a rotation angle of the motor 59a is connected to the rotation axis of the motor 59a.

The joint 53b (or the pivoted section 54b between the joints 53b and 53c) and the joint 53c (or the pivoted section 54c between the joints 53c and 53d) can be rotated with a similar configuration.

That is, the joint 53b is connected to a pulley 58b inside the motor box 56 through wires 57b and 57b which are inserted inside the joints 53c and 53d and winded around the pulley 58b, the pulley 58b being connected to a rotation axis of a motor 59b, and the rotation axis of the motor 59b being connected to an encoder 60b which functions as a sensor for detecting (acquiring) a rotation angle of the motor 59b.

Furthermore, the joint 53c is connected to a pulley 58c inside the motor box 56 through wires 57c and 57c which are inserted inside the joint 53d and winded around the pulley 58c, the pulley 58c being connected to a rotation axis of a motor 59c, and the rotation axis of the motor 59c being connected to an encoder 60c.

The motors 59a to 59c inside the motor box 56 are connected to a motor drive circuit 41B inside the control section 10B through signal lines within a cable 67, and are driven with driving signals supplied from the motor drive circuit 41B.

Output signals from the encoders 60a to 60c will be inputted to an A/D conversion circuit 43B inside the control section 10B through the signal lines within the cable 67. The A/D converted digital signals from the A/D conversion circuit 43B will be inputted to a determination section 12B and a control circuit 42B.

A signal with respect to the angle for bending (turning) the pivoted sections 54a to 54c among the plurality of joints that configure the bending section 55, corresponding to an instruction input operation by the user, will be inputted to the control circuit 42B as an instruction input signal through a joystick 44B, which is a specific example of the instruction input device 9B.

The control circuit 42B, in a usual (normal) case, takes a signal of a difference value derived by subtracting the encoder output signal from the instruction input signal as a new instruction input signal, and outputs this new instruction input signal to the motor drive circuit 41B. Then the motor drive circuit 41B will output driving signals corresponding to such instruction input signal to the motors 59a to 59c.

The control device 8A as shown in FIG. 8 has the configuration for drive controlling the two motors 37a and 37b, whereas the control device shown in FIG. 9 has the configuration for drive controlling the three motors 59a to 59c.

As with the configuration of the control device 8A shown in FIG. 8, the control device 8B shown in FIG. 9 also includes a motor characteristic storage section 13B and a setting section 14B. The motor characteristic storage section 13B and the setting section 14B have similar functions to the motor characteristic storage section 13A and the setting section 14A as described with reference to FIG. 8.

Moreover, a memory section 15B, a replacement section 16B and a calculation section 17B as arranged in the determination section 12B have similar functions to the memory section 15A, the replacement section 16A and the calculation section 17A as arranged in the determination section 12A, respectively.

With respect to an operation in a case when the joints 33, 33, ..., 33 of the bending section 25 are drive-controlled using the motor unit 35 of the endoscope 2 shown in FIG. 8, the operation will be approximately the same as that in the case of FIG. 2 considering that the active mechanism 7A is replaced with motors 37a and 37b, and the sensor 11A is replaced with the encoders 38a and 38b.

Likewise, with respect to an operation of the treatment instrument 3, the operation will be approximately the same as that in the case of FIG. 2, considering that the above-mentioned motors 37a and 37b are replaced with motors 59a to 59c, and the encoders 38a and 38b are replaced with encoders 60a to 60c.

Thus, according to the present embodiment, when the active mechanism or the drive section is actively drive-operated with a driving signal while the operation status is detected by the sensor and the detected sensor value is used in drive controlling the active mechanism or the drive section, even in such case where the sensor value is found to be abnormal due to noise, etc., the drive control can be executed based on the valid sensor value acquired at the time just before the abnormal status has occurred, whereby the operation can be continued without being forced to stop under abnormal termination. Therefore, operability for a user can be enhanced.

Second Embodiment

Now, with reference to FIG. 10, an endoscope treatment system 1B that includes a second embodiment of the present invention will be described. In the endoscope treatment system 1B shown in FIG. 10, the treatment instrument 3 in the endoscope treatment system 1 of FIG. 1 is an electric energy treatment instrument, for instance, which has an energy treatment section 52a arranged at a distal end portion thereof, the energy treatment section 52a functioning to perform treatments using electric energy such as high frequency electric energy, for example.

The present embodiment is provided with a decision section. The decision section decides to execute or stop the determination operation by the determination section according to a used or unused status of an energy output device that outputs electric energy (hereinafter to be referred to simply as energy), the energy output device being an external device of the manipulator 20.

Moreover, this treatment instrument 3 has the active mechanism 7B which is provided with the bending section 55 arranged around a posterior end of a distal end portion thereof, as shown in FIG. 9, for example.

This endoscope treatment system 1B has an energy output instruction input device (to be referred to simply as instruction input device) 61 which provides an instruction input on energy output, and an energy output device 62 which outputs energy such as high frequency electric energy, in response to the instruction input on the energy output.

This energy will be applied through the energy treatment section 52a at the distal end of the treatment instrument 3 to a treatment target region, such as a lesioned part, inside a body, whereby a treatment such as resection, by energy can be performed.

In the present embodiment, the energy output device 62 outputs ON/OFF information on energy output to the determination section 12. Based on the ON/OFF information on energy output as being information on an operation environment including a used or unused status of the energy output device, the determination section 12 automatically determines whether the determination operation for determining whether or not the sensor value is normal is to be executed or not.

Specifically, in a period where the energy output is ON (i.e. in an operation environment where the energy output device is used), the determination operation for determining whether or not the sensor value is valid is executed as in the case of the first embodiment, whereas in a period where the energy output is OFF (i.e. in an operation environment where the energy output device is not used), the determination operation for determining whether or not the sensor value is valid is not executed (i.e. the determination operation is stopped).

The present embodiment is a case that copes with a situation where the operation is carried out with the sensor value of the sensor 11A or 11B being at a sufficiently highly reliable state (even without the validity determination) while energy is not outputted from the energy output device 62, while there is a possibility, only during the period where energy is outputted, that the sensor value becomes susceptible to the energy from the energy output device 62 for the energy could be taken as noise. The rest of the configuration is the same as that in the first embodiment.

Next, an operation in the present embodiment will be described with reference to a flow chart of FIG. 11. The following description will be about a case of an operation in terms of the treatment instrument 3.

Figure 10:
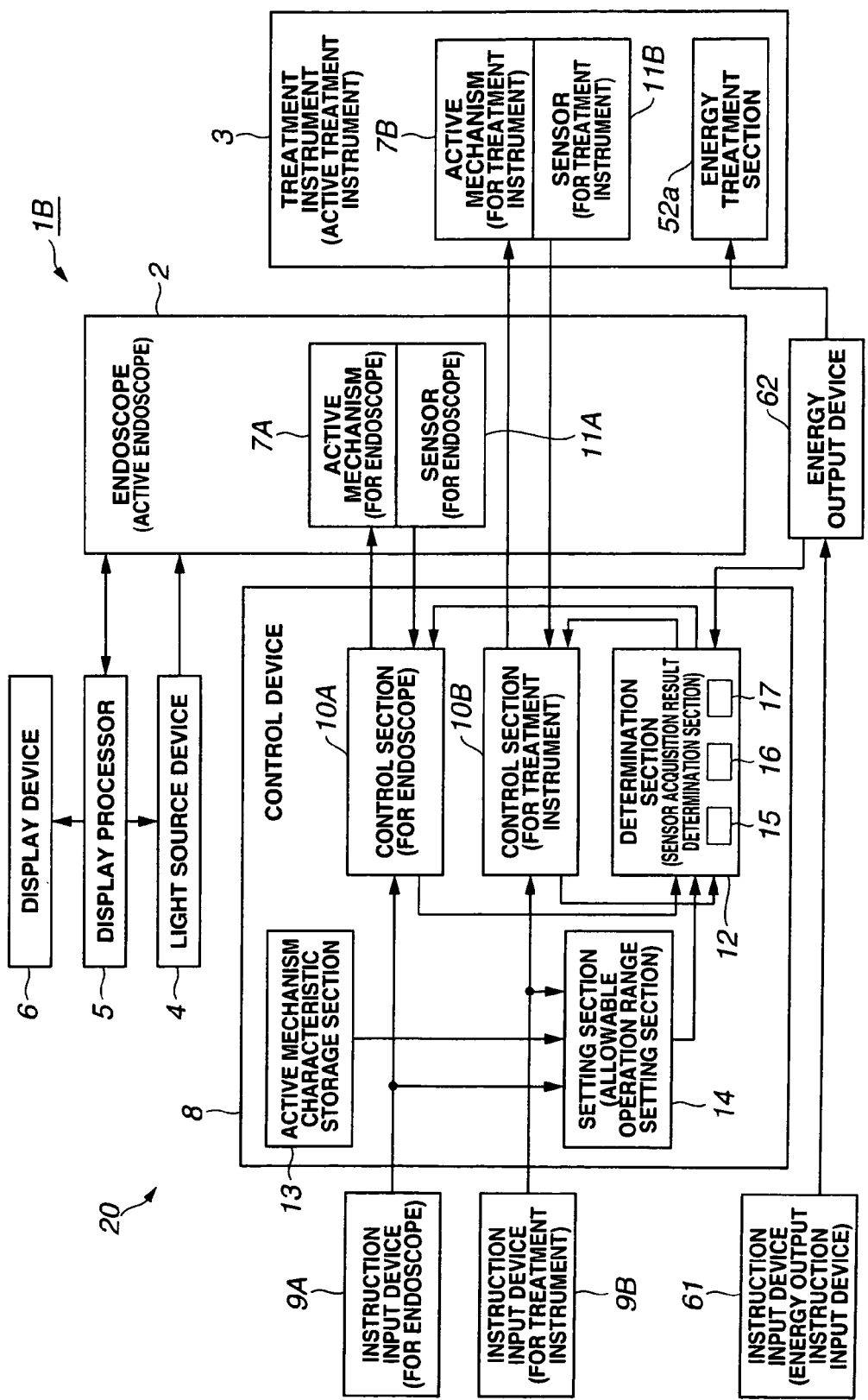
FIG. 10 is a block diagram showing an overall configuration of an endoscope treatment system that includes a second embodiment of the present invention.

The operation starts when power is supplied to the endoscope treatment system 1B shown in FIG. 10. Then at an initial step S21 in FIG. 11, the determination section 12 determines whether the instruction input device 61 has requested the energy output device 62 for energy output, i.e. whether or not an energy output instruction is ON.

When the output instruction is ON, the determination section 12, at step S22, acquires a sensor value from the sensor 11B. (Here, it is also possible to arrange such that at an initial point when the output instruction is switched from OFF to ON, the sensor value is acquired before the energy output.)

Then according to the acquired sensor value, the determination section 12, at a subsequent step S23, executes a determination process for determining the validity of the sensor value (i.e. determining whether or not there is an error).

Then at a subsequent step S24, the control section 10B generates a driving signal for driving the active mechanism 7B based on the determination result by the determination section 12, and thus controls the active mechanism 7B.

Specifically, when it is determined that the sensor value is valid, the control section 10B, at step S25, generates (controls) a driving signal for driving the active mechanism 7B using that sensor value. On the other hand, when the determination section 12 determines that there is an error and thus outputs a replacement signal, the control section 10B, at step S26, takes that replacement signal as a sensor value to generate a driving signal for driving the active mechanism 7B. This process may be executed by the replacement section 16 instead of the control section 10B.

Meanwhile, at step S21, when the output instruction is not ON, i.e. when the output instruction is OFF, the determination section 12, at step S27, acquires a sensor value from the sensor 11B.

Then after the process at step S27, the operation proceeds to step S25 where a driving signal is generated based on the acquired sensor value.

In this way, when the output instruction is OFF, the determination process for determining the validity is not executed with respect to the acquired sensor value, while the driving signal is generated based on that acquired sensor value.

Figure 11:
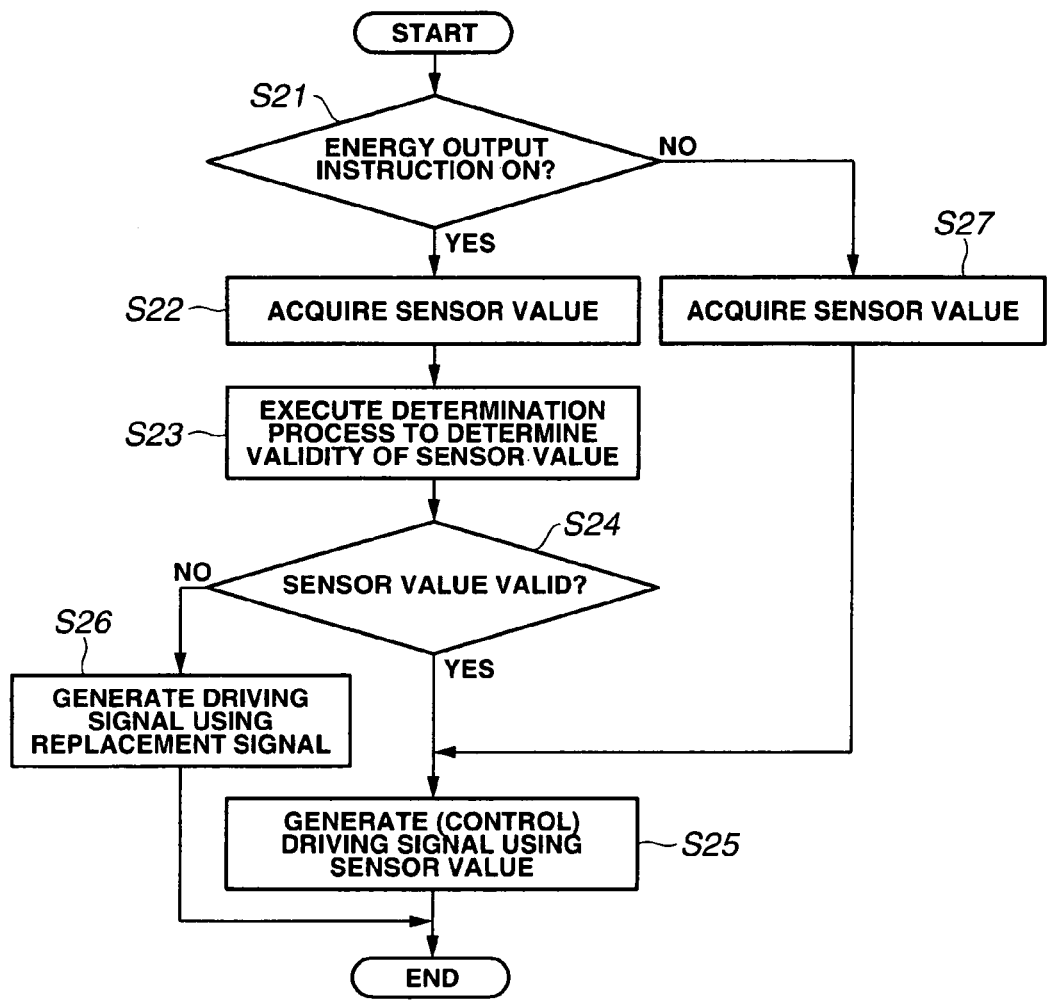
FIG. 11 is a flow chart showing contents of processes related to energy output, according to the second embodiment.

According to the present embodiment, by executing the processes as shown in FIG. 11, while energy is not outputted from the energy output device 62, it is possible to eliminate the determination process with respect to the validity of the sensor value and the subsequent process in the case when the sensor value is found to be an error through the validity determination process. Thereby, possible decrease in responsiveness can be prevented.

Other advantageous effects that can be achieved in the present embodiment are similar to those in the first embodiment.

Although the present embodiment adopts decision means that automatically decides that the determination process with respect to validity of the sensor value should be executed or not based on the ON or OFF status of the output instruction, it is also possible to arrange such that a user can choose whether the determination process with respect to validity of the sensor value should be executed or not through an input device or the like, which is not shown.

Moreover, although the example of the operation as described with reference to FIG. 11 is about the operation in the case of drive controlling the active mechanism 7B of the treatment instrument 3, similar operation can be applied in the case of drive controlling the active mechanism 7A of the endoscope 2.

Furthermore, as in the configuration shown in FIG. 8, for example, in the case when the determination section 12A takes in the sensor values from the encoders 38a and 38b through the A/D conversion circuit 43, it is possible to arrange such that the output signals of the encoders 38a and 38b taken as the sensor values in forms of pulse signals can be determined whether they are valid or not based on whether the periods or frequencies of the pulse signals are within predetermined ranges (this arrangement can also be applied to the case of FIG. 9).

Figure 12:
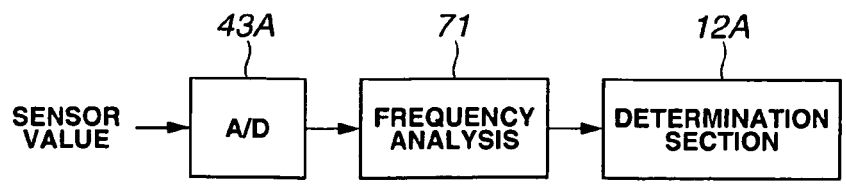
FIG. 12 is a configuration diagram of a section that determines validity of a sensor value based on whether or not an output of the sensor value is within a predetermined frequency band.

Accordingly, as shown in FIG. 12, for example, it is possible to arrange such that a value of the sensor value having been A/D converted by the A/D conversion circuit 43A is inputted to the determination section 12A through a frequency analysis section 71 (or a filter section with a plurality of filters having different pass bands), and the determination section 12A determines whether the sensor value is valid or not based on the analysis by the analysis section 71, etc. showing whether the input signal directed to the determination section 12A is within a predetermined frequency band.

For example, considering a case where an energy output device or the like is used, frequency of the energy form the energy output device will usually become higher than that of the pulse signals outputted from the encoders 38a and 38b as being based on rotation.

In such case, it is possible to arrange such that the sensor value will be determined as invalid or an error due to noise brought in by the energy output device 62, if the input signal analyzed by the frequency analysis section 71, etc. is found to be in a higher band side than the predetermined frequency band (which can be considered appropriate as a frequency band of a sensor value).

In this way, it is possible to have the validity of the sensor value determined based on the frequency analysis, etc., of the detection signal of the sensor. Then, as described above, in such event when an error is determined, the driving control may be executed using the sensor value acquired at the time just before the error has been determined.

The arrangement, the process, etc., related to frequency analysis as described above can also be applied to a case in which a sensor value is to be taken in not through the A/D conversion circuit 43A.

The above-described embodiments, etc., have been described as the cases of the manipulator having the bending section 25 or 55 with the plurality of turnable joints 33 or 53 to 53*d*. However, it is obvious that the above-described embodiments, etc. can be applied to a case of driving a manipulator with a single joint. Moreover, the above-described embodiments, etc. can be applied to a case of driving an actuator with a plurality of joints.

Furthermore, the above-described embodiments, etc. can be applied to a case of a manipulator which is configured in such a way that the joints 33, etc. can be rotated around an insertion axis (arranged in a longitudinal direction) of the insertion section 21.

Moreover, the operation status signal is not limited to the one that includes information on three of the angle, the angular velocity and the angular acceleration, but can include information on the angle only, or information on the angle and the angular velocity. In other words, it is possible to arrange such that the calculation section 17 calculates only the angular velocity or only the angular acceleration based on the angle, and the determination section determines whether the angle and the angular velocity or the angular acceleration are within allowable operation ranges.

Embodiments which can be configured by partially combining the above-described embodiments, etc. belong to the present invention as well.

What is claimed is:

1. A manipulator comprising:
a drive section which electrically drives a turnable joint;
an instruction input section which executes instruction input for rotating the joint;
a driving signal generation section which generates a driving signal for driving the drive section in response to the instruction input;
a sensor which detects an operation status of the joint or the drive section in time series;
a setting section which sets an allowable operation range within which the drive section is operable in a case when the drive section is driven with the driving signal;
a determination section which determines whether an operation status signal corresponding to the operation status is within the allowable operation range, the operation status signal at least including a detection signal detected by the sensor;
a control section which, in a case when the operation status signal is determined as being within the allowable operation range, generates a driving signal for a time after the determination using the detection signal; and
a replacement section which, in a case when the operation status signal is determined as deviating from the allowable operation range, replaces the detection signal with a previous detection signal having been determined as being within the allowable operation range just before a time the operation status signal has been determined as deviating from the allowable operation range, and generates a driving signal for a time after the determination of deviance.

2. The manipulator according to claim 1, further comprising
a memory section which stores the detection signal detected by the sensor in time series.

3. The manipulator according to claim 2, wherein
the sensor includes an encoder which, when a rotary drive section configuring the drive section is rotated, detects an angle of the rotation, the manipulator further comprising
a calculation section which calculates an angular velocity value based on an angle value taken as the detection signal acquired by the encoder, the angular velocity value included in the operation status signal.

4. The manipulator according to claim 3, wherein
the calculation section also calculates an angular acceleration value which is included in the operation status signal.

5. The manipulator according to claim 2, wherein
the control section, in a case when the operation status signal including the detection signal is determined as being within the allowable operation range, generates a driving signal for the time after the determination through the use of a difference value derived by subtracting the detection signal from an instruction input signal corresponding to the instruction input as a new instruction input signal, and
the replacement section, in a case when the operation status signal including the detection signal is determined as deviating from the allowable operation range, reads out from the memory section a previous detection signal, having been determined as being within the allowable operation range just before the time when deviance has been determined, and generates a driving signal for the time after the determination of deviance through the use of a difference value derived by subtracting the previous detection signal from the instruction input signal as a new instruction input signal.

6. The manipulator according to claim 2, wherein
the replacement section, in a case when the operation status signal is determined as deviating from the allowable operation range, reads out the detection signal from the memory section to replace the detection signal with the previous detection signal, while the replacement section also uses a replacement signal in which an amount of change, which can be estimated from a change in the previous detection signal from a time when the previous detection signal was detected to a time of the determination, is added to the previous detection signal, to generate a driving signal for the time after the determination of deviance.

7. The manipulator according to claim 1, further comprising
a decision section which decides to execute or stop a determination operation by the determination section according to a used or unused status of an energy output device that outputs electric energy, the energy output device being arranged outside the manipulator.

8. The manipulator according to claim 1, wherein
the sensor includes an encoder which, when a rotary drive section configuring the drive section is rotated, detects an angle of the rotation, the manipulator further comprising
a calculation section which calculates an angular velocity value based on an angle value taken as the detection signal acquired by the encoder, the angular velocity value included in the operation status signal.

9. The manipulator according to claim 8, wherein the calculation section also calculates an angular acceleration value which is included in the operation status signal.

10. The manipulator according to claim 9, wherein
the determination section determines whether all of the angle value, the angular velocity value and the angular acceleration value which are included in the operation status signal are within the allowable operation ranges having been set in terms of angle, angular velocity and angular acceleration, respectively, and
the replacement section replaces the detection signal with the previous detection signal in a case when at least one of the angle value, the angular velocity value and the angular acceleration value is found to be deviating from the allowable operation range.

11. The manipulator according to claim 9, wherein
the determination section determines whether all of the angle value, the angular velocity value and the angular acceleration value which are included in the operation status signal are within the allowable operation ranges having been set in terms of angle, angular velocity and angular acceleration, respectively, and
the replacement section, in a case when at least one of the angle value, the angular velocity value and the angular acceleration value is determined as deviating from the allowable operation range, generates a driving signal for the time after the determination of deviance through the use of a difference value derived by subtracting a previous angle value, having been determined as being within the allowable operation range just before the time when deviance has been determined, from an instruction input signal corresponding to the instruction input as a new instruction input signal.

12. The manipulator according to claim 8, wherein
the determination section determines whether the angle value and the angular velocity value which are included in the operation status signal are within the allowable operation ranges having been set in terms of angle and angular velocity, respectively, and
the replacement section replaces the detection signal with the previous detection signal in a case when at least one of the angle value and the angular velocity value is found to be deviating from the allowable operation range.

13. The manipulator according to claim 8, wherein
the determination section determines whether the angle value and the angular velocity value which are included in the operation status signal are within the allowable operation ranges having been set in terms of angle and angular velocity, respectively,
the control section, in a case when a determination result indicates that the angle value and the angular velocity value are within the allowable operation ranges, generates a driving signal for the time after the determination through the use of a difference value derived by subtracting the angle value from an instruction input signal corresponding to the instruction input as a new instruction input signal, and
the replacement section, in a case when the determination result indicates that the angle value and the angular velocity value are deviating from the allowable operation ranges, generates a driving signal for the time after the determination of deviance through the use of a difference value derived by subtracting a previous angle value, having been determined as being within the allowable operation range just before the time when deviance has been determined, from the instruction input signal as a new instruction input signal.

14. The manipulator according to claim 1, wherein
the sensor includes an encoder which, when a rotary drive section configuring the drive section is rotated, detects an angle of the rotation, and
the determination section determines whether the operation status signal is within the allowable operation range based on a determination whether a pulse signal, which is to be outputted according to an angle of rotation of the rotary drive section as acquired by the encoder, is within a predetermined frequency band.

15. The manipulator according to claim 1, wherein
the control section, in a case when the operation status signal including the detection signal is determined as being within the allowable operation range, generates a driving signal for the time after the determination through the use of a difference value derived by subtracting the detection signal from an instruction input signal corresponding to the instruction input as a new instruction input signal, and
the replacement section, in a case when the operation status signal including the detection signal is determined as deviating from the allowable operation range, generates a driving signal for the time after the determination of deviance through the use of a difference value derived by subtracting a previous detection signal, having been determined as being within the allowable operation range just before the time when deviance has been determined, from the instruction input signal as a new instruction input signal.

16. The manipulator according to claim 1, further comprising
a correction section which corrects a shift amount between the detection signal in a case where the operation status signal including the detection signal is determined as deviating from the allowable operation range and the previous detection signal for replacement, in order to generate a driving signal for the time after the determination.

17. The manipulator according to claim 1, wherein
the replacement section, in a case when the operation status signal is determined as deviating from the allowable operation range, replaces the detection signal with the previous detection signal, while the replacement section also adds an amount of change, which can be estimated from a change in the previous detection signal from a time when the previous detection signal was detected to a time of the determination, to the previous detection signal, in order to generate a driving signal for the time after the determination of deviance.

18. The manipulator according to claim 17, further comprising
a correction section which corrects a shift amount between the detection signal in a case where the operation status signal including the detection signal is determined as deviating from the allowable operation range and the replacement signal, in order to generate a driving signal for the time after the determination.

19. The manipulator according to claim 1, further comprising
a bendable bending section having a plurality of the joints being connected thereto.

20. The manipulator according to claim 19, wherein
the bending section is arranged at an elongated flexible insertion section which is to be inserted into a body.

21. The manipulator according to claim 20, wherein
the insertion section is an insertion section of an endoscope where an objective optical system is arranged at a distal end portion of the insertion section, or an insertion section of a treatment instrument where a treatment section is arranged at the distal end portion of the insertion section.

22. A method of controlling a manipulator comprising:

an instruction input step for executing instruction input for rotating a turnable joint to a target angle;

a first driving step for driving the joint via a drive section with a driving signal based on an instruction input signal from the instruction input step;

a setting step for setting an allowable operation range allowed in a case of driving the joint;

an acquiring step for acquiring, while the joint is rotating according to a driving signal, an angle of rotation of the joint as a sensor value in time series;

a determining step for determining whether the sensor value acquired in the acquiring step is within the allowable operation range; and a second driving step in which, in a case when the sensor value is determined as being within the allowable operation range, a driving signal for a time after the determination is generated using the sensor value, and in a case when the sensor value is determined as deviating from the allowable operation range, a driving signal for a time after the determination is generated by replacing the sensor value with a previous sensor value having been determined as being within the allowable operation range just before the time when deviance is determined.

23. The method of controlling a manipulator according to claim 22, wherein in the second driving step, in a case when the sensor value is determined as being within the allowable operation range, a difference value derived by subtracting the sensor value from the instruction input signal is used as a new instruction input signal to generate a driving signal for the time after the determination, and in a case when the sensor value is determined as deviating from the allowable operation range, a difference value derived by subtracting the previous sensor value, having been determined as being within the allowable operation range just before the time when deviance is determined, from the instruction input signal is used as a new instruction input signal to generate a driving signal for the time after the determination.

24. The method of controlling a manipulator according to claim 22, further comprising a calculating step for calculating an angular velocity value and an angular acceleration value based on the sensor value acquired in the acquiring step, wherein in the determining step, it is determined whether the angular velocity value and the angular acceleration value as calculated in the calculating step are within allowable operation ranges having been set in terms of angular velocity and angular acceleration, respectively, and in the second driving step, in a case when at least one of the acquired sensor value on the angle, the angular velocity value and the angular acceleration value is determined as deviating from the allowable operation range, the sensor value is replaced with the previous sensor value.

* * * * *